United States Patent
Nakada et al.

(10) Patent No.: US 7,183,448 B2
(45) Date of Patent: Feb. 27, 2007

(54) AZEOTROPIC COMPOSITION, COMPRISING 1, 1, 1, 3,3-PENTAFLUOROPROPANE AND 1, 1, 1-TRIFLUORO-3-CHLORO-2-PROPENE, METHOD OF SEPARATION AND PURIFICATION OF THE SAME, AND PROCESS FOR PRODUCING 1, 1, 1,3,3-PENTAFLOROPROPANE AND 1, 1, 1-TRIFLUORO-3-CHLORO-2-PROPENE

(75) Inventors: Tatsuo Nakada, Osaka (JP); Masayoshi Imoto, Osaka (JP); Takashi Shibanuma, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/831,598

(22) PCT Filed: Nov. 10, 1999

(86) PCT No.: PCT/JP99/06255

§ 371 (c)(1),
(2), (4) Date: Jul. 17, 2001

(87) PCT Pub. No.: WO00/29361

PCT Pub. Date: May 25, 2000

(65) Prior Publication Data

US 2005/0085674 A1    Apr. 21, 2005

(30) Foreign Application Priority Data

Nov. 13, 1998 (JP) .................................. 10-323496

(51) Int. Cl.
C07C 17/04 (2006.01)
C07C 17/02 (2006.01)
C09K 21/08 (2006.01)

(52) U.S. Cl. ...................... 570/164; 570/153; 570/156; 570/165; 570/166; 570/167; 570/168; 570/170; 570/169; 570/177; 203/81; 203/82; 203/84; 252/181.11; 252/182.12

(58) Field of Classification Search ................ 570/164, 570/165, 166, 167, 168, 169, 156, 153, 170, 570/177; 203/81, 82, 84; 252/182.11, 182.12
See application file for complete search history.

(56) References Cited

U.S. PATENT DOCUMENTS 5,616,819 A    4/1997    Boyce et al.

FOREIGN PATENT DOCUMENTS

| DE | 19716337 | 11/1997 |
|---|---|---|
| DE | 19716337 A1 | 11/1997 |
| EP | 864554 | 9/1998 |
| EP | 0864554 A1 | 9/1998 |
| EP | 0877009 A1 | 11/1998 |
| EP | 0885863 | 12/1998 |
| EP | 1067106 A1 | 1/2001 |
| GB | 2313118 A | 11/1997 |
| JP | 9-241189 | 9/1997 |
| JP | 9241188 | 9/1997 |
| JP | 9241189 A | 9/1997 |
| JP | 9183740 | 7/1998 |
| WO | 9727163 | 7/1931 |
| WO | WO9601797 | 1/1996 |
| WO | 97/14307 | 7/1997 |
| WO | WO9727163 | 7/1997 |
| WO | WO9724307 | 10/1997 |
| WO | WO9737955 | 10/1997 |
| WO | 9948849 | 9/1999 |
| WO | WO9948849 | 9/1999 |

*Primary Examiner*—Elvis O. Price
(74) *Attorney, Agent, or Firm*—Birch, Stewart, Kolasch & Stewart, LLP

(57) ABSTRACT

A mixture comprising at least 1,1,1,3,3-pentafluoropropane and 1,1,1-trifluoro-3-chloro-2-propene is subjected to a distillation operation, and thereby, a distillate comprising an azeotropic composition consisting substantially of 1,1,1,3, 3-pentafluoropropane and 1,1,1-trifluoro-3-chloro-2-propene is obtained and a bottom product comprising 1,1,1,3, 3-pentafluoropropane or 1,1,1-trifluoro-3-chloro-2-propene which each is separated and purified.

13 Claims, 1 Drawing Sheet

AZEOTROPIC COMPOSITION, COMPRISING 1, 1, 1, 3,3-PENTAFLUOROPROPANE AND 1, 1, 1-TRIFLUORO-3-CHLORO-2-PROPENE, METHOD OF SEPARATION AND PURIFICATION OF THE SAME, AND PROCESS FOR PRODUCING 1, 1, 1,3,3-PENTAFLOROPROPANE AND 1, 1, 1-TRIFLUORO-3-CHLORO-2-PROPENE

This application is the national phase under 35 U.S.C. § 371 of PCT International Application No. PCT/JP99/06255 which has an International filing date of Nov. 10, 1999, which designated the United States of America and was published in English.

1. Technical Field

The present invention relates to an azeotropic composition consisting of 1,1,1,3,3-pentafluoropropane (which is referred to also as "R-245fa" hereinafter) and 1,1,1-trifluoro-3-chloro-2-propene (which is referred to also as "R-1233zd" hereinafter), and a process of separation and purification of R-245fa or R-1233zd from a mixture comprising at least R-245fa and R-1233zd. R-245fa is a useful compound which is considered a compound which is not likely to cause a substantial ozone depletion, and R-245fa can be used as, for example, an HFC forming agent, a refrigerant, a heat transfer medium and a propellant.

2. Background Art

There is described in International Publication No. WO96/01797 that R-245fa can be easily produced by fluorinating 1,1,1,3,3-pentachloropropane with hydrogen fluoride (which is referred to also as "HF") in the presence of a catalyst. In this reaction, R-1233zd is formed as an intermediate and mixed as an impurity into the objective, i.e. R-245fa.

Further, Japanese Patent Kokai Publication No. 9-183740 (A) discloses a process for fluorinating 1,1,1,3,3-pentachloropropane in a vapor phase. A reaction product is a mixture comprising R-1233zd and R-245fa also in this process. Further, Japanese Patent Kokai Publication No. 9-241188 (A) discloses a process for producing 1,1,1,3,3-pentachloropropane by fluorinating R-1233zd in a liquid phase. A reaction product is a mixture comprising R-1233zd and R-245fa also in this process. Further, there is a process for producing 1,1,1,3,3-pentafluoropropane by fluorinating 1,1,1,3-tetrachloropropene and/or 1,1,3,3-tetrachloropropene. R-245fa and R-1233zd is comprised in the reaction product also in this process.

As described in the above, in any one of the fluorinating reactions, the reaction product containing R-245fa as an object contains R-1233zd as an impurity. Therefore, it is necessary to separate and purify R-245fa from the reaction product containing the impurity. Further, it is desirable to recover R-1233zd from such a reaction product from the viewpoint of production cost and so on.

In this specification, the term "separation and purification" is used in the sense of separating and concentrating a key component (for example, R-245fa) when a mixture stream comprises two or more specific key components (for example, R-245fa and R-1233zd) in a ratio of a concentration "a" of one key component (for example, R-245fa) to a concentration "b" of the other key component (for example, R-1233zd), i.e. "a/b" is subjected to a given process (for example, a distillation), and thereby other stream is obtained of which ratio of the concentration of said one key component (for example, R-245fa) to the concentration of said other key component (for example, R-1233zd) is increased to "a'/b'" (wherein "a'/b'" is larger than "a/b").

DISCLOSURE OF INVENTION

As described in the above, in order to separate and purify R-245fa, it is necessary to remove R-1233zd contained in the reaction product. R-1233zd has two geometrical isomers (E) and (Z). The boiling point of (E) isomer is 20.5° C. and the boiling point of (Z) is 35° C., while the boiling point of R-245fa is about 15° C. Therefore, since the boiling point of (E) isomer of the two isomers of R-1233zd is close to that of R-245fa, it is particularly difficult to separate (E) isomer from R-245fa.

Removal of olefin such as R-1233zd and so on has been attempted. For example, in International Publication No. WO97/37955, there is described a process of separation by a chlorine addition. However, in the process wherein R-1233zd is separated as a chlorinated compound, R-1233zd cannot be reused for a production process of R-245fa. That is, the formation of chlorinated compound contributes to a decrease of the recovery of R-1233zd, and therefore, the production cost is increased.

As described in the above, an effective method for separating R-1233zd which is contained in the reaction product from the reaction to produce R-245fa, has not yet been found so far.

The present invention has been accomplished in the light of the circumstances as described above, of which object is to provide a process of separation and purification of R-245fa and/or R-1233zd from a mixture comprising at least R-245fa and R-1233zd, in which process R-1233zd is not changed to other compound(s), i.e. R-1233zd can be recovered and reused.

The inventors have made extensive studies on a process of separation of R-1233zd contained in R-245fa and found for the first time that R-245fa and R-1233zd form an azeotropic composition in which R-245fa:R-1233zd is about 63:37 almost at the atmospheric pressure, and then completed the present invention. Herein, the isomer of R-1233zd which forms the azeotropic composition is (E) isomer. Hereinafter, (E) isomer of R-1233zd is referred to also as "(E)R-1233zd". So far, it has not been known that these form an azeotropic composition. It should be noted that these compounds form an azeotropic mixture even under pressure.

Thus, in the first aspect, the present invention provides an azeotropic composition (or an azeotropic mixture) which consists substantially of 1,1,1,3,3-pentafluoropropane and 1,1,1-trifluoro-3-chloro-2-propene. In this azeotropic composition, a 1,1,1,3,3-pentafluoropropane/1,1,1-trifluoro-3-chloro-2-propene molar ratio is in the range of 64/36 to 62/38 at an azeotropic temperature of 14° C. at the atmospheric pressure.

The azeotropic composition is useful as a reflux when a distillation operation is carried out in order to separate one component of 1,1,1,3,3-pentafluoropropane and 1,1,1-trifluoro-3-chloro-2-propene from a mixture comprising them (e.g. a product of a reaction to produce 1,1,1,3,3-pentafluoropropane).

In the second aspect, the present invention provides a process of separation and purification of 1,1,1,3,3-pentafluoropropane or 1,1,1-trifluoro-3-chloro-2-propene from a mixture comprising at least 1,1,1,3,3-pentafluoropropane and 1,1,1-trifluoro-3-chloro-2-propene.

Namely, the process is:
1) a process of separation and purification of 1,1,1,3,3-pentafluoropropane characterized by:
subjecting a mixture comprising at least 1,1,1,3,3-pentafluoropropane and 1,1,1-trifluoro-3-chloro-2-propene to a distillation operation; and thereby
obtaining a distillate comprising an azeotropic composition consisting substantially of 1,1,1,3,3-pentafluoropropane and 1,1,1-trifluoro-3-chloro-2-propene; and
obtaining a bottom product comprising 1,1,1,3,3-pentafluoropropane which does not substantially contain 1,1,1-trifluoro-3-chloro-2-propene; or
2) a process of separation and purification of 1,1,1-trifluoro-3-chloro-2-propene characterized by:
subjecting a mixture comprising at least 1,1,1,3,3-pentafluoropropane and 1,1,1-trifluoro-3-chloro-2-propene to a distillation operation; and thereby
obtaining a distillate comprising an azeotropic composition consisting substantially of 1,1,1,3,3-pentafluoropropane and 1,1,1-trifluoro-3-chloro-2-propene; and
obtaining a bottom product comprising 1,1,1-trifluoro-3-chloro-2-propene which does not substantially contain 1,1,3,3-pentafluoropropane.

The compound to be separated and purified depends on an R-245fa/(E)R-1233zd ratio in a mixture, i.e. a feed, which is subjected to the distillation operation.

In a case where the R-245fa/(E)R-1233zd ratio in the feed is larger than the R-245fa/(E)R-1233zd ratio in the azeotropic mixture at an operation pressure of a distillation operation, for example, in a case where the ratio of (E)R-1233zd in the feed is smaller than 37 mol % at the atmospheric pressure, a bottom product comprising R-245fa which does not substantially contain (E)R-1233zd is obtained by a distillation operation in which a distillate comprising an azeotropic composition of R-245fa and (E)R-1233zd is obtained and a part of the azeotropic composition is used as a reflux.

In this case, (Z) isomer of R-1233zd (hereinafter which is referred to also as "(Z)R-1233zd") is contained in the bottom product. In order to obtain R-245fa of higher purity by separating (Z)R-1233zd, the bottom product may be subjected to a fractional distillation to separate R-245fa from (Z)R-1233zd.

To the contrary, in a case where the R-245fa/(E)R-1233zd ratio in the feed is smaller than the R-245fa/(E)R-1233zd ratio in the azeotropic mixture at an operation pressure of a distillation operation, for example, in a case where the ratio of (E)R-1233zd in the feed is larger than 37 mol % at the atmospheric pressure, a bottom product comprising (E)R-1233zd which does not substantially contain R-245fa is obtained by a distillation operation in which a distillate comprising an azeotropic composition of R-245fa and (E)R-1233zd is obtained and a part of the azeotropic composition is used as a reflux.

Also in this case, the bottom product contains (Z)R-1233zd. (E)R-1233zd and (Z)R-1233zd can be separated by subjecting the bottom product to a fractional distillation.

Upon separating and purifying R-245fa or (E)R-1233zd, the feed may further contain hydrogen fluoride. In that case, a distillate consists substantially of hydrogen fluoride and an azeotropic composition consisting substantially of R-245fa and (E)R-1233zd. There is a case that the bottom product contains hydrogen fluoride. In a case where the bottom product contains hydrogen fluoride, if it is desired to separate hydrogen fluoride, it may be separated by a method conventionally employed, such as a distillation, an extraction, water washing, a liquid-liquid phase separation or the like.

BEST MODE FOR CARRYING OUT THE INVENTION

Figure 1:
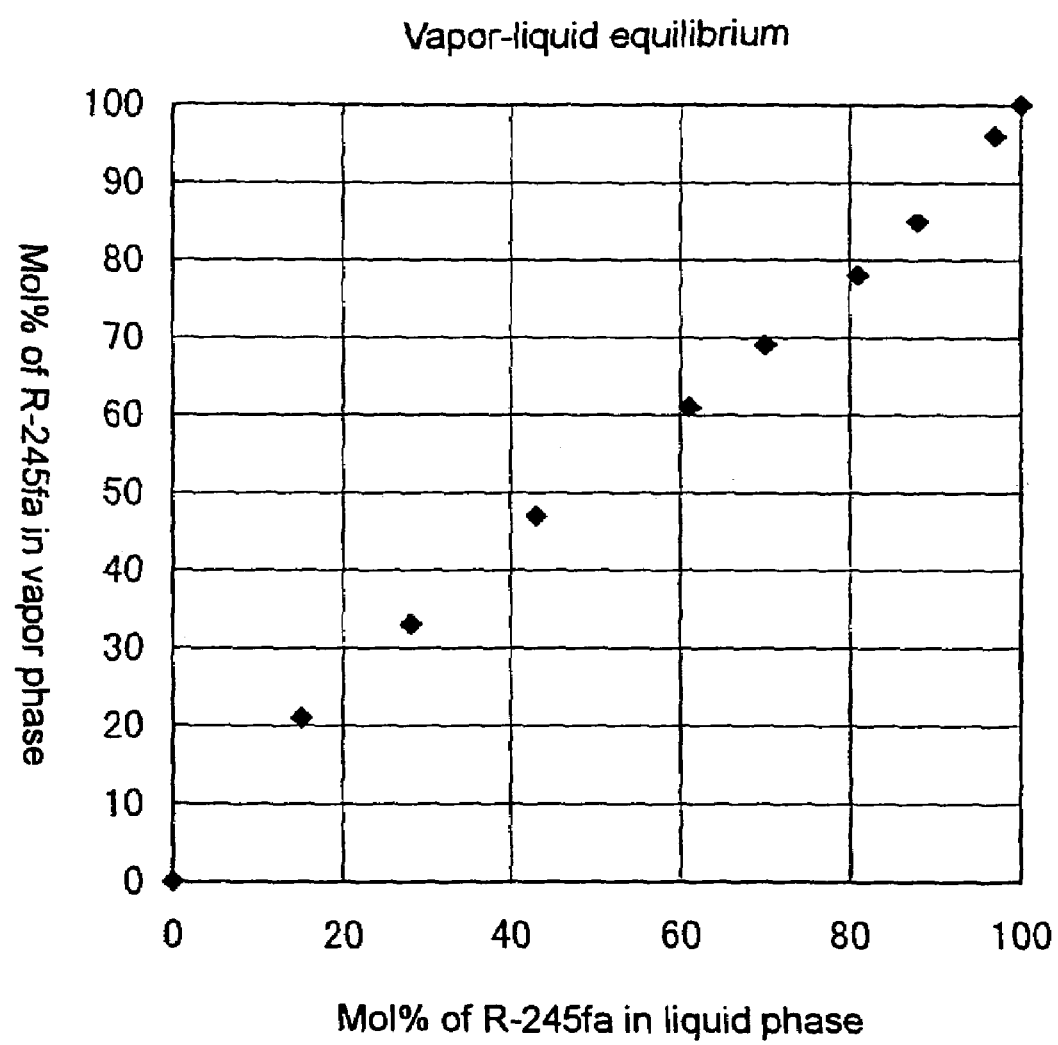
FIG. 1 is a graph showing a vapor-liquid equilibrium relationship of 1,1,1,3,3-pentafluoropropane and 1,1,1-trifluoro-3-chloro-2-propene.

The separation and purification process of the present invention can be performed in a batch process or a continuous process using a distillation apparatus conventionally used. Generally, it is preferably performed in the continuous process. The type of a distillation apparatus is not limited to a particular one, and a general distillation apparatus such as a packed column, a plate column or the like may be used. Operation conditions for the distillation may be appropriately selected by the skilled person in this art taking into consideration the distillation apparatus which is used, the azeotropic point, utility limitations and so on. After condensation, the distilled azeotropic composition is preferably used as it is as a reflux in the distillation operation.

The operation pressure is preferably, for example, in the range of 0 kgf/cm$^2$-G to 10 kgf/cm$^2$-G. The number of plates of a plate column may be appropriately selected depending on the composition of the mixture fed thereto, and the degree of separation of the distillate and the bottom product (for example, an impurity concentration), a reflux ratio and so on.

The process of separation and purification of the present invention includes a process wherein an objective compound is obtained by being distilled off and being condensed after an azeotropic composition is completely distilled off, as well as a process wherein an objective compound is obtained in the form of a bottom product. Distilling off the objective has an advantage that higher boiling compound(s) is not contained therein.

The process of separation and purification of the present invention is preferably carried out by subjecting a mixture comprising 1,1,1-trifluoro-3-chloro-2-propene and 1,1,1,3,3-pentafluoropropane to a distillation operation, which mixture is a reaction product obtained by fluorinating the following:
1) 1,1,1,3,3-pentachloropropane;
2) 1,1,1-trifluoro-3-chloro-2-propene;
3) 1,1,1,3-tetrachloropropene and/or 1,1,3,3-tetrachloropropene; or any combination of two or three of 1), 2) and 3) as a feed with hydrogen fluoride in the presence of an appropriate catalyst. When the fluorination is carried out in a vapor phase, it is desirable that the resulting vapor phase composition is condensed, and then subjected to the distillation operation. It should be noted that in the mixture obtained in such a manner, (E)R-1233dz and (Z)R-1233zd generally exist at a molar ratio of about 10:1.

The mixture may comprise hydrogen fluoride. In that case, hydrogen fluoride as well as an azeotropic composition consisting substantially of 1,1,1-trifluoro-3-chloro-2-propene and 1,1,1,3,3-pentafluoropropane is distilled off. Hydrogen fluoride may be, for example, unreacted hydrogen fluoride in the above reaction.

Alternatively, unreacted hydrogen fluoride is removed from the mixture as a reaction product by liquid-liquid separation, and then, the layer rich in organic material is subjected to the distillation operation, whereby the separation and purification of 1,1,1,3,3-pentafluoropropane or 1,1,1-trifluoro-3-chloro-2-propene is carried out.

When carrying out the process of separation and purification of the present invention, if the fluorination mentioned in the above is a liquid phase reaction, a distillation apparatus may be incorporated with a reactor vessel. More specifically, this is exemplified by an embodiment in which produced R-245fa is withdrawn as a bottom product from a distillation column which also functions as a reactor vessel in a case where one of the above feeds 1), 2) and 3) or the combination of two or more thereof is fluorinated in an HF solvent.

The process of separation and purification of the present invention can be applied to a process for producing 1,1,1,3,3-pentafluoropropane by fluorinating one of the above feeds 1), 2) and 3) or the combination of two or more thereof with hydrogen fluoride, and provides a process for producing 1,1,1,3,3-pentafluoropropane characterized by:

subjecting a reaction product comprising 1,1,1,3,3-pentafluoropropane and 1,1,1-trifluoro-3-chloro-2-propene obtained by a fluorination process to a distillation operation; and thereby distilling off an azeotropic composition comprising 1,1,1,3,3-pentafluoropropane and 1,1,1-trifluoro-3-chloro-2-propene; and obtaining a bottom product comprising 1,1,1,3,3-pentafluoropropane which does not substantially contain 1,1,1-trifluoro-3-chloro-2-propene.

It should be noted that in the production process, the reaction product may contain unreacted hydrogen fluoride. In that case, there can be provided a process for producing 1,1,1,3,3-pentafluoropropane characterized by:

subjecting a reaction product comprising 1,1,1-trifluoro-3-chloro-2-propene, 1,1,1,3,3-pentafluoropropane and hydrogen fluoride to a distillation operation; and thereby obtaining a distillate comprising hydrogen fluoride and an azeotropic composition consisting substantially of 1,1,1-trifluoro-3-chloro-2-propene and 1,1,1,3,3-pentafluoropropane; and obtaining a 1,1,1,3,3-pentafluoropropane bottom product which does not substantially contain 1,1,1-trifluoro-3-chloro-2-propene. In that case, the bottom product may further comprises hydrogen fluoride. In such a case, 1,1,1,3,3-pentafluoropropane and hydrogen fluoride can be separated by a distillation, an extraction, water washing or the like.

The azeotropic composition of R-245fa and R-1233zd which is obtained as a distillate in the process of separation and purification of 1,1,1,3,3-pentafluoropropane of the present invention, can be recycled to a fluorination process in which R-1233zd is contained in a feed and/or a reaction product. This enables R-1233zd which is distilled off, to be used effectively in the production of 1,1,1,3,3-pentafluoropropane. Such a production is carried out, for example, according to the production process provided by the present invention as described in the above.

Further, the azeotropic composition of R-245fa and R-1233zd which is obtained as a distillate in the process of separation and purification of 1,1,1-trifluoro-3-chloro-2-propene of the present invention, can be recycled to the fluorination process in which R-1233zd is involved as a product. This enables R-1233zd which is distilled off, to be used effectively in the production of 1,1,1-trifluoro-3-chloro-2-propene. Such a production is carried out, for example, by fluorinating the feed 1) or 3) referred in the above with hydrogen fluoride.

The process disclosed in Japanese Kokai Publication No. 9-24188, Japanese Kokai Publication No. 9-183740 and International Publication No. WO/96/01797 can be made reference as to the process for producing R-245fa by fluorinating one of the above feeds 1), 2) and 3), or the combination of two or more thereof.

As described in the above, the process of separation and purification of the present invention is preferably applied to an effluent from a reaction system in which R-245fa is produced. However, the process can be applied to any mixture from other source as long as the mixture comprises R-245fa and (E)R-1233zd or comprises R-245fa, (E)R-1233zd and HF. Further, in a case where the mixture contains other component(s) as well as R-245fa, (E)R-1233zd and HF, the other component(s) behaves with the azeotropic composition as a distillate or behaves with R-245fa or (E)R-1233zd as a bottom product, depending upon its affinity for R-245fa, (E)R-1233zd and HF and the operation conditions of the distillation process. Depending on the conditions, the other component(s) behaves with both of the distillate and the bottom product.

INDUSTRIAL APPLICABILITY

As described in the above, according to a process of separation and purification of the present invention in which a distillation process wherein a distillate is an azeotropic composition of the present invention is employed, purified R-245fa or (E)R-1233zd can be obtained as a bottom product from a mixture comprising R-245fa and (E)R-1233zd effectively. Further, the process of separation and purification of the present invention is useful from the viewpoint of recovery and recycling of a feed since the azeotropic composition withdrawn as a distillate is returned to a fluorination process as a reflux and R-245fa is produced by fluorinating (E)R-1233zd in the azeotropic composition.

EXAMPLES

Example 1

The vapor-liquid equilibrium of R-245fa and (E)R-1233zd was measured at the atmospheric pressure in the following manner.

A predetermined amount of R245fa and (E)R-1233zd is introduced into an Othmer vapor-liquid equilibrium measuring apparatus and sufficiently refluxed. Thereafter, samples were obtained from the still portion (the liquid phase) and the reflux (the vapor phase), and compositions of them were analyzed by means of gas chromatography. The results (molar fraction of R-245fa in the liquid phase and the vapor phase) are shown in Table 1 and FIG. 1. The balance is (E)R-1233zd.

TABLE 1

| Liquid phase (mol %) | Vapor phase (mol %) | Temperature (° C.). |
|---|---|---|
| 15 | 21 | 20 |
| 28 | 33 | 18 |
| 43 | 47 | 16 |
| 63 | 63 | 14 |
| 81 | 78 | 14.3 |
| 88 | 85 | 14.6 |
| 97 | 96 | 15 |

Example 2

1257 grams of a mixture of R-245fa and R-1233zd containing 1 mol % of (E)R-1233zd which mixture was a reaction product obtained by fluorinating 1,1,1,3,3-pentachloropropane was rectified by using an Oldershaw distillation column with 40 plates under an operation pressure (top pressure) of 0 kgf/cm$^2$-G at a top temperature of 14° C. An azeotropic composition of (E)R-1233zd and R-245fa was distilled off from the top and R-1233zd and R-245fa were withdrawn together in a total amount of 33 g. As a result, 1220 g of R-245fa of which purity is more than 99.9 mol % was obtained from the bottom of the distillation column.

Example 3

1366 grams of a mixture of R-245fa and R-1233zd containing 10 mol % of (E)R-1233zd which mixture was a reaction product obtained by fluorinating 1,1,1,3,3-pentachloropropane was rectified by using an Oldershaw distillation column with 40 plates under an operation pressure (top pressure) of 0 kgf/cm$^2$-G at a top temperature of 14° C. An azeotropic composition of (E)R-1233zd and R-245fa was distilled off from the top and (E)R-1233zd and R-245fa were withdrawn together in a total amount of 340 g. As a result, 1021 g of R-245fa of which purity is more than 99.9 mol % was obtained from the bottom of the distillation column.

Example 4

1355 grams of a mixture of R-245fa and (E)R-1233zd containing 1 mol % of R-245fa which mixture was a reaction product obtained by fluorinating 1,1,1,3,3-pentachloropropane in a vapor phase was rectified by using an Oldershaw distillation column with 40 plates under an operation pressure (top pressure) of 0 kgf/cm$^2$-G at a top temperature of 14° C. An azeotropic composition of (E)R-1233zd and R-245fa was distilled off from the top and R-245fa and R-1233zd were withdrawn together in a total amount of 41 g. As a result, 1310 g of R-1233zd of which purity is more than 99.9 mol % was obtained from the bottom of the distillation column.

The invention claimed is:

1. An azeotropic composition consisting of 1,1,1,3,3-pentafluoropropane and 1,1,1-trifluoro-3-chloro-2-propene.

2. The azeotropic composition according to claim 1 in which a molar ratio of 1,1,1,3,3-pentafluoropropane/1,1,1-trifluoro-3-chloro-2-propene of the azeotropic composition is in the range of 64/36 to 62/38.

3. A process of separation and purification of 1,1,1,3,3-pentafluoropropane characterized by:
    subjecting a mixture which comprises at least 1,1,1,3,3-pentafluoropropane and 1,1,1-trifluoro-3-chloro-2-propene to a distillation operation; and thereby
    obtaining a distillate comprising an azeotropic composition consisting substantially of 1,1,1,3,3-pentafluoropropane and 1,1,1-trifluoro-3-chloro-2-propene; and
    obtaining a bottom product comprising 1,1,1,3,3-pentafluoropropane which dose not substantially contain 1,1,1-trifluoro-3-chloro-2-propene.

4. A process of separation and purification of 1,1,1-trifluoro-3-chloro-2-propene characterized by:
    subjecting a mixture which comprises at least 1,1,1,3,3-pentafluoropropane and 1,1,1-trifluoro-3-chloro-2-propene to a distillation operation; and thereby
    obtaining a distillate comprising an azeotropic composition consisting substantially of 1,1,1,3,3-pentafluoropropane and 1,1,1-trifluoro-3-chloro-2-propene; and
    obtaining a bottom product comprising 1,1,1-trifluoro-3-chloro-2-propene which dose not substantially contain 1,1,1,3,3-pentafluoropropane.

5. A process of separation and purification of 1,1,1,3,3-pentafluoropropane characterized by:
    subjecting a mixture which comprises at least 1,1,1,3,3-pentafluoropropane, 1,1,1-trifluoro-3-chloro-2-propene and hydrogen fluoride to a distillation operation; and thereby
    obtaining a distillate consisting substantially of hydrogen fluoride and an azeotropic composition of 1,1,1,3,3-pentafluoropropane and 1,1,1-trifluoro-3-chloro-2-propene; and
    obtaining a bottom product comprising 1,1,1,3,3-pentafluoropropane which dose not substantially contain 1,1,1-trifluoro-3-chloro-2-propene.

6. The process of separation and purification of 1,1,1,3,3-pentafluoropropane according to claim 5 in which the bottom product further comprises hydrogen fluoride.

7. A process of separation and purification of 1,1,1-trifluoro-3-chloro-2-propene characterized by:
    subjecting a mixture which comprises at least 1,1,1,3,3-pentafluoropropane, 1,1,1-trifluoro-3-chloro-2-propene and hydrogen fluoride to a distillation operation; and thereby
    obtaining a distillate consisting substantially of hydrogen fluoride and an azeotropic composition of 1,1,1,3,3-pentafluoropropane and 1,1,1-trifluoro-3-chloro-2-propene; and
    obtaining a bottom product comprising 1,1,1-trifluoro-3-chloro-2-propene which dose not substantially contain 1,1,1,3,3-pentafluoropropane.

8. The process of separation and purification of 1,1,1-trifluoro-3-chloro-2-propene according to claim 7 in which the bottom product further comprises hydrogen fluoride.

9. The process of separation and purification according to any one of claims 3 to 8, in which the mixture which is subjected to the distillation operation is a reaction product of a fluorination of 1,1,1,3,3-pentachloropropane.

10. The process of separation and purification according to any one of claims 3 to 8, in which the mixture which is subjected to the distillation operation is a reaction product of a fluorination of 1,1,1-trifluoro-3-chloro-2-propene.

11. The process of separation and purification according to any one of claims 3 to 8, in which the mixture which is subjected to the distillation operation is a reaction product of a fluorination of 1,1,1,3-tetrachloropropene and/or 1,1,3,3-tetrachloropropene.

12. A process for producing 1,1,1,3,3-pentafluoropropane, in which the distillate comprising the azeotropic composition of 1,1,1,3,3-pentafluoropropane and 1,1,1-trifluoro-3-chloro-2-propene which is obtained by the distillation operation in any one of claims 3, 5 and 6, is recycled to a fluorination process in which 1,1,1-trifluoro-3-chloro-2-propene is involved as a feed and/or a reaction product.

13. A process for producing 1,1,1-trifluoro-3-chloro-2-propene, in which the distillate comprising the azeotropic composition of 1,1,1,3,3-pentafluoropropane and 1,1,1-trifluoro-3chloro-2-propene which is obtained by the distillation operation in any one of claims 4, 7 and 8, is recycled to a fluorination process in which 1,1,1-trifluoro-3-chloro2-propene is involved as a reaction product.

* * * * *